United States Patent [19]

Okada et al.

[11] Patent Number: 5,431,637
[45] Date of Patent: Jul. 11, 1995

[54] ENDOTRACHEAL SUCTION CATHETER

[75] Inventors: Yosuke Okada; Nobuaki Suzuki, both of Shizuoka, Japan; Curtis D. Kinghorn, Ferguson, Mo.

[73] Assignee: Sherwood Medical Company, St. Louis, Mo.

[21] Appl. No.: 923,191

[22] Filed: Jul. 31, 1992

[51] Int. Cl.⁶ .................................. A61M 25/00
[52] U.S. Cl. .................................. 604/264; 604/280
[58] Field of Search ............... 604/264, 265, 268, 280, 604/266, 281, 282, 283, 284, 28, 30, 34; 606/191, 197, 198, 199

[56] References Cited

U.S. PATENT DOCUMENTS

| | | | |
|---|---|---|---|
| 2,691,373 | 10/1954 | Bried | 604/265 |
| 3,136,316 | 6/1964 | Beall | 128/350 |
| 3,516,410 | 6/1970 | Hakin | 604/268 |
| 3,599,642 | 8/1971 | Tindel | 128/351 |
| 3,618,613 | 11/1971 | Schulte | 128/348 |
| 3,659,611 | 5/1972 | Miller | 128/351 |
| 3,670,726 | 6/1972 | Mahon et al. | 128/188 |
| 3,777,757 | 12/1973 | Gray et al. | 604/280 |
| 3,858,615 | 1/1975 | Weigl | 138/121 |
| 3,945,385 | 3/1976 | Sackner | 128/350 R |
| 3,963,856 | 6/1976 | Carlson et al. | 174/47 |
| 4,275,724 | 6/1981 | Behrstock | 128/207.14 |
| 4,593,690 | 6/1986 | Sheridan et al. | 128/207.15 |
| 4,717,379 | 1/1988 | Ekholmer | 604/280 |
| 4,781,678 | 11/1988 | de Court et al. | 604/266 |
| 4,852,564 | 8/1989 | Sheridan et al. | 128/292.27 |
| 4,950,232 | 8/1990 | Ruzicka et al. | 604/268 |
| 4,969,878 | 11/1990 | Schmidt et al. | 604/264 |
| 4,987,895 | 1/1991 | Heimlich | 128/207.14 |
| 5,024,220 | 6/1991 | Holmgreen et al. | 128/207.18 |

FOREIGN PATENT DOCUMENTS

| | | | |
|---|---|---|---|
| 2554352 | 5/1985 | France | 604/280 |
| 0408449 | 1/1925 | Germany | 604/280 |
| 0666587 | 10/1938 | Germany | 604/264 |
| 2528273 | 10/1976 | Germany | 604/265 |
| 3608943 | 4/1987 | Germany | 604/264 |
| 3735927 | 5/1989 | Germany | 604/280 |

Primary Examiner—C. Fred Rosenbaum
Assistant Examiner—Manuel Mendez
Attorney, Agent, or Firm—Montgomery W. Smith; Curtis D. Kinghorn; Ari M. Bai

[57] ABSTRACT

A suction catheter is disclosed having a tubular, bellowed flexible proximal or patient contacting end creating a rigidity to not permit bending and twisting during the catheter's insertion and operation, a flexibility to prevent injuring a patient's trachea or bronchial tube and having a good suction efficiency. A lumen leads to openings in the catheter made at the bellowed proximal end that fluidly connects the lumen with the exterior of the catheter.

16 Claims, 12 Drawing Sheets

ENDOTRACHEAL SUCTION CATHETER

BACKGROUND OF THE INVENTION

1. Field of the Invention

This device relates to a suction catheter, and more particularly to a endotracheal suction catheter.

2. Description of Related Art

A typical conventional endotracheal suction catheter is shown in FIGS. 1 and 2. The suction catheter is adapted to remove deposits in a trachea or bronchial tube through suction force generated by a reduced or vacuum pressure in the catheter lumen. The suction catheter is inserted through a trachea and a bronchial tube. Thereafter, vacuum pressure is applied to the catheter lumen which vacuum pressure is transferred to the deposit causing it to be moved into the catheter lumen. According to the ordinary use of the suction catheter, some medical operations such as supplying oxygen are temporarily stopped as the endotracheal suction catheter is positioned and during the deposit removing operation.

As best shown in FIG. 1, suction catheters 1 typically have an elongated tube portion 2, that is usually a tubular member made of polyvinyl chloride (PVC) or similar material enclosing a lumen 3 extending substantially from the proximal end 4 to the distal end 5 of catheter 1. Proximal end 4 is inserted into a body lumen A of a patient such as the trachea or a bronchial tube (see FIG. 2). Lumen 3 is connected to a pressure reducing means such as a vacuum source (not shown) at the distal end 5 of catheter 1 for reducing pressure in the lumen 3 of the catheter 1.

A hand assisting part 6 is formed at the distal end 5 of the catheter 2. Hand assisting part 6 allows the operator of catheter 1 to move and manipulate catheter 1 during insertion and removal of the catheter 1 from the body lumen A of a patient as well as while catheter 1 is in use in the patient's body. Often the hand assisting part 6 is made integrally with the suction catheter 1 and may be shaped as a small partly swelled bulb.

An end opening 7 is formed in the proximal end 4 along the axis of tube portion 2. End opening 7 places the lumen 3 directly in fluid communication with body lumen A. An annular flange 8 having an outer diameter larger than the outer diameter of tube portion 2 is located around the proximal end 4 of catheter 1. The central axis of flange 8 is aligned with the axis of tube portion 2 and flange 8 extends radially away from tube portion 2.

There are several side holes 9 formed in the tube portion 2 of the catheter 1 near flange 8 fluidly connecting lumen 3 with the exterior of tube portion 2. Side holes 9 are located along tube portion 2 near but on the distal side of flange 8. Side holes 9 combine with end opening 7 to form a suction mouth at distal end 5. A suction control hole 10 is formed at the distal end 5 of catheter 1 near the hand assisting part 6. Suction control hole 10 extends from lumen 3 to the exterior of tube portion 2. When suction control hole 10 is open, vacuum pressure in lumen 3 escapes through control hole 10. When vacuum pressure in lumen 3 escapes through control hole 10, the vacuum pressure is prevented from being available at end opening 7 and side holes 9. By placing a thumb or other finger over suction control hole 10, vacuum pressure in lumen 3 is prevented from escaping from lumen 3 at control hole 10, thereby presenting vacuum pressure to end hole 7 and side holes 9. Covering and uncovering suction control hole 10 controls the vacuum pressure within lumen 3.

FIG. 2 is a schematic cross-section view of the prior art catheter of FIG. 1 in use in a body lumen A. The proximal end 4 is inserted into the body lumen A and vacuum pressure is applied to lumen 3 at distal end 5. When suction control hole 10 is closed as described above, an air pressure difference is created between lumen 3 and the body lumen A causing air in body lumen A to flow in layers toward proximal end 4. This air flowing in layers is divided into two streams. One stream enters end opening 7 and flows straight through lumen 3 to the source of vacuum pressure. The other stream flows through the gap between the outer periphery of the flange 8 and body lumen A and enters lumen 3 through the side holes 9. The flowing air causes deposits in the body lumen A near flange 8 to be removed and brought into lumen 3 through end opening 7 and side holes 9. Once the deposits are in lumen 3, they are subsequently moved out of the catheter 1 at the distal end 5 by being caught or engulfed in the air flowing through lumen 3.

Characteristics desirable for the suction catheters are:

(a) Ordinarily, the catheter is quickly operated, so it must have a strength or rigidity and stiffness sufficient to prevent the suction catheter from bending and twisting during insertion and operation;

(b) the catheter should be able to suck and effectively remove deposits through a suction mouth at the proximal end;

(c) because the proximal end is apt to strike a trachea or bronchial tube during insertion and operation, it is preferable to make the proximal end of the catheter as soft and flexible as possible to avoid producing an injury and bleeding to the trachea or bronchial tube; and, (d) also, it is desirable that the shape of the proximal end not stick the trachea or bronchial tube resulting in injuries and bleeding.

SUMMARY OF THE INVENTION

The catheter of the instant invention has an elongated tube enclosing a lumen. The proximal end of the catheter has a bellowed or corrugated tube shape. This shape is formed by a series of connected annular "ridges" and "valleys".

The catheter includes an end opening, aligned with the major axis of the lumen extending through the catheter. The end opening fluidly connects the proximal end of the catheter with the lumen. In addition, side holes fluidly connect the "valleys" of the tubular shaped proximal end with the main lumen. In one embodiment, every "valley" contains at least one side hole. In a variation of this, a plurality of side holes may be placed in at least one "valley". In a further variation of this, not every "valley" will contain a side hole and in those "valleys" containing side holes, the number and location of the side holes may be varied.

According to the present device, because the proximal end of the suction catheter has a bellowed tubular shape, the proximal end has greater flexibility than the straight tubular part. Accordingly, when the catheter is inserted into the body lumen, shock, and corresponding injury, to the inner face of the body lumen or bronchial tube is reduced.

In addition, because there are several side holes formed and placed at the predetermined positions in the "valleys" of the bellowed tubular part, when vacuum pressure is applied to the lumen, layers of air flow through the end hole and side holes in similar fashion to that of prior art suction catheters. Part of the air flows along the surface of the "ridges" of the bellowed tubular part so that the air enters the side holes and evacuates out of the catheter through the lumen. The other part of the air flows through the end hole into and through the lumen.

The present device is devised to have the desired characteristics and solve the problems described above, among others that will occur to those skilled in the art.

It is a primary object of the instant invention to provide an endotracheal suction catheter that will not injure or damage the bronchial tube or tracheal airway passage during insertion and use.

It is another object of the instant invention to provide a endotracheal suction catheter that may be quickly inserted and operated.

It is another object of the instant invention to provide an endotracheal suction catheter that resists bending and twisting during insertion and use.

It is yet another object of the instant invention to provide an endotracheal suction catheter that has a suction mouth at the distal end.

It is another object of the instant invention to provide a suction catheter that may be made of one material.

The instant invention will be described in detail with reference to the attached drawings where corresponding elements are referred to by identical reference numbers.

DETAILED DESCRIPTION OF THE INVENTION

Figure 1:
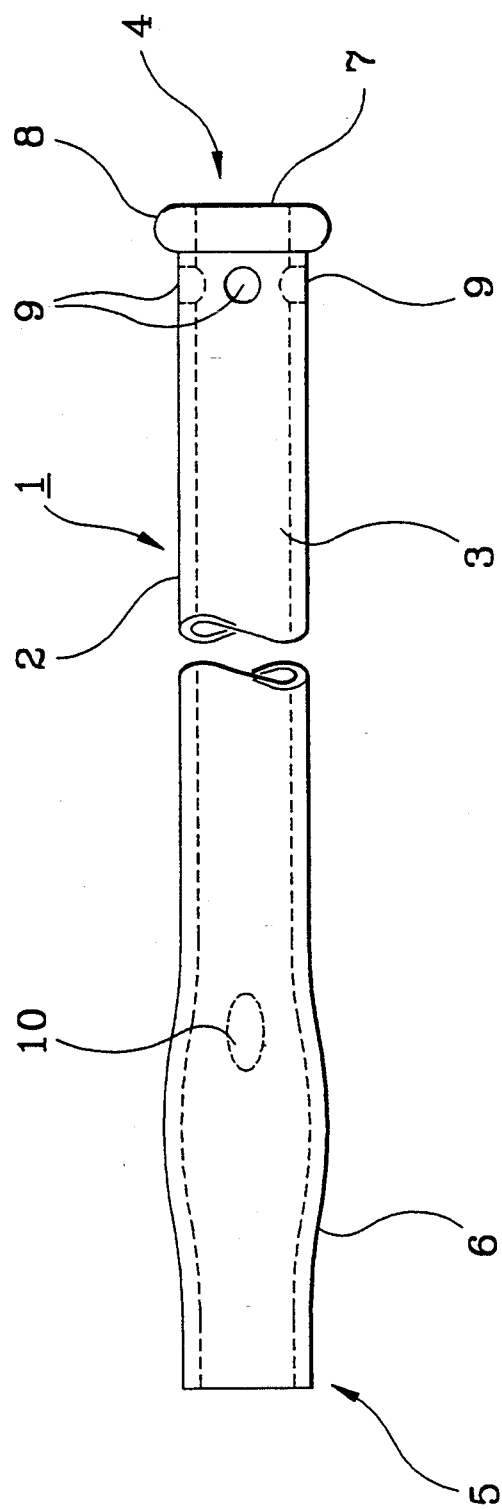
FIG. 1 is a schematic elevational view showing one embodiment of a conventional suction catheter.
Figure 2:
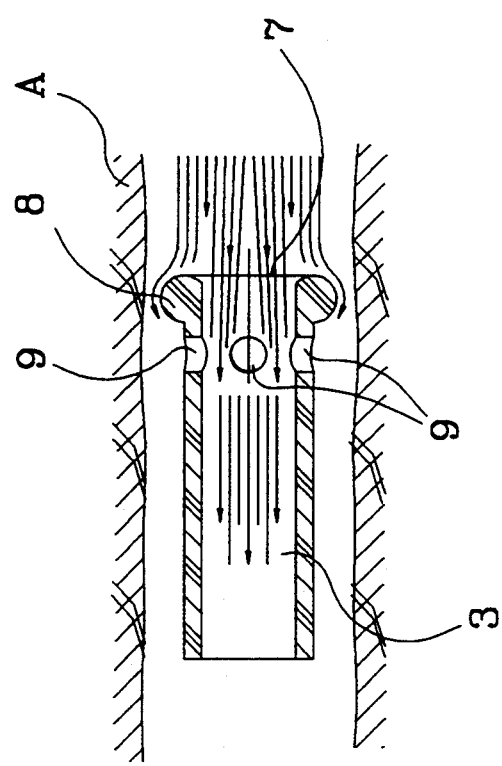
FIG. 2 is a cross-sectional view showing the conventional apparatus of FIG. 1 in use.
Figure 3:
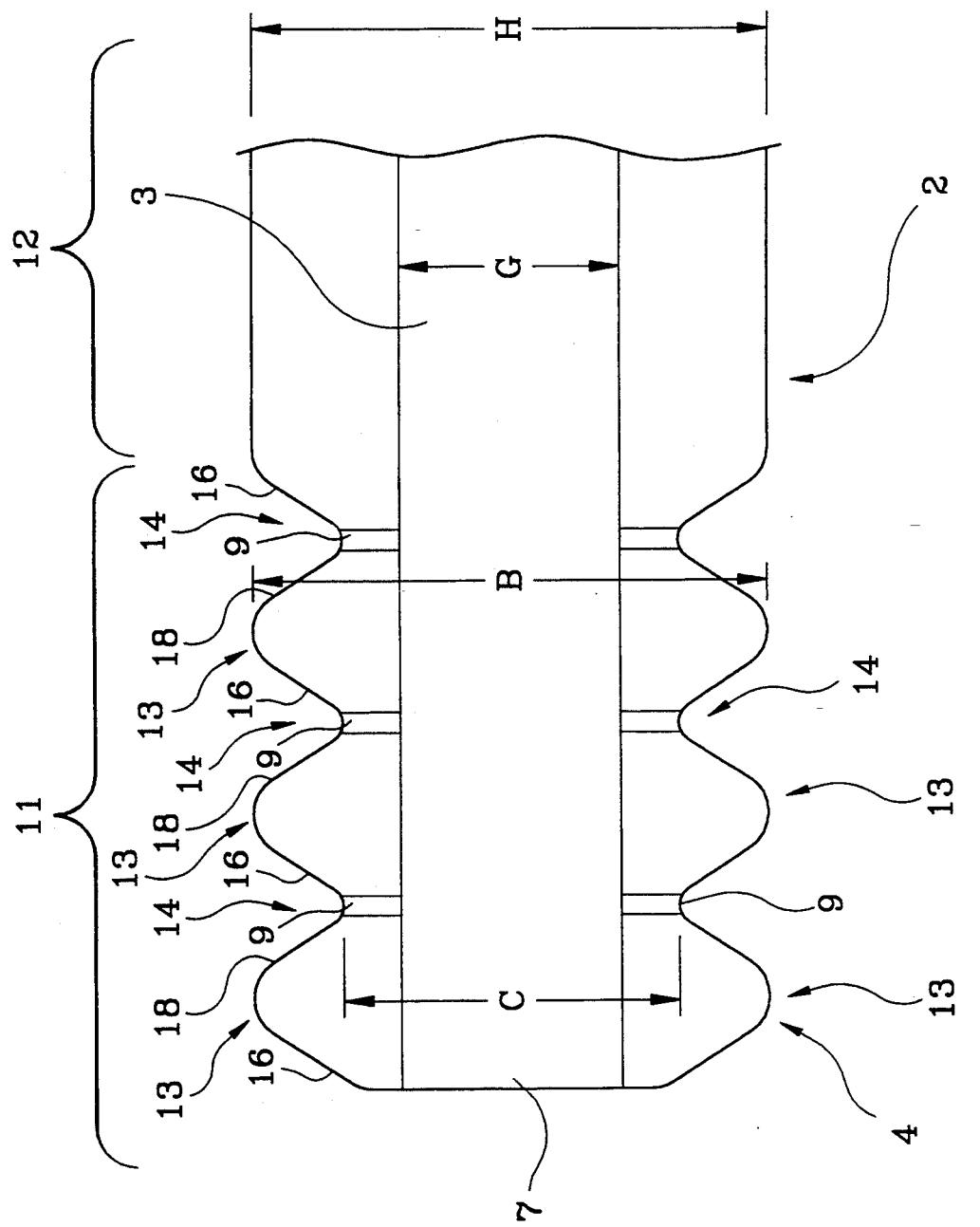
FIG. 3 is a cross-sectional view of the proximal end of the catheter according to one embodiment of the present device.

FIG. 3 is a sectional view of a portion of one embodiment of the suction catheter 1 of the instant invention, near its patient contacting or proximal end 4. The suction catheter 1 is preferably made of a soft PVC material having a rigidity a little stiffer than that of a soft or flexible PVC tube used in conventional suction catheters such as that shown in FIG. 1. As is well known, it is possible to select a suitable rigidity for catheter 1 relatively at will because PVC may be made in many degrees of rigidity extending from hard or rigid to soft or flexible. Consequently, it is possible to manufacture a catheter 1 of an appropriate PVC material to satisfy an important requirement of performance for the device that it not bend or twist when inserted into the body lumen A.

The proximal end 4 of the catheter 1 is constructed of a bellowed tubular part 11 extending proximally from straight tubular portion 12 of catheter 1. As viewed in cross-section, bellowed tubular part 11 consists of several sequential "ridges" 13 and "valleys" 14 giving the bellowed tubular part 11 a corrugated appearance. The "ridges" 13 and "valley"s 14 are annular and extend around the central elongated axis of lumen 3. The bellowed tubular part 11 may be easily made by a thermal mold process or by other processes that will occur to those skilled in the art.

Figure 4:
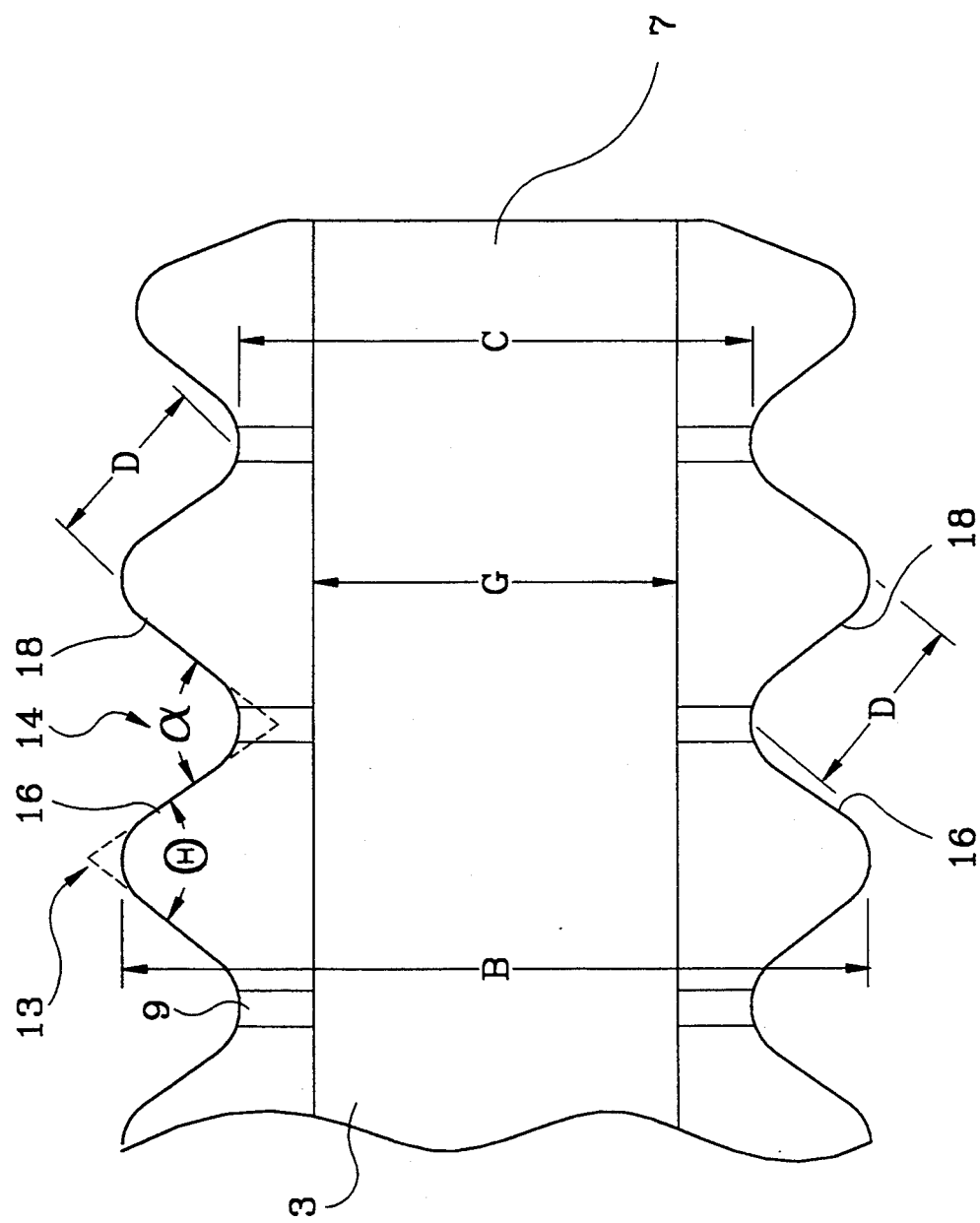
FIG. 4 is an enlarged cross-sectional view of the "ridges" and "valleys" of the device of FIG. 3.

As shown in FIG. 4, each of the "ridges" 13 and "valleys" 14 are made of a series of annular proximal flat pieces 16 and distal flat pieces 18. Flat pieces 16,18 are connected along a common edge at an angle $\theta$ to each other to make a "ridge" 13. Flat pieces 18,16 are connected along a common edge at an angle $\alpha$ to make a "valley" 14. A series of alternating "ridges" 13 and "valleys" 14 extend from the proximal end 4 throughout the bellowed tubular part 11 to the straight tubular part 12. The preferred angle for both $\theta$ and $\alpha$ is approximately 90° but other angles may be used as well, including, but not limited to 60°. Further, differing angles for $\theta$ and $\alpha$ may be used as desired.

When viewed in cross-section, each "ridge" will have a "major" diameter B defined as the largest cross-sectional distance across the annular "ridge" 13 and a "minor" diameter C defined as the smallest cross-sectional distance across the annular "valley" 14. A series of "ridges" are connected along their edges of "minor" diameter C to form the alternating series of "ridges" 13 and "valleys"14.

In the preferred embodiment, the width D of each proximal flat piece 16 and its neighboring distal flat piece 18 are identical. The width of a flat piece 16,18 is defined as the shortest distance from a connecting point between a proximal flat piece 16 and a distal flat piece 18 across the respective flat piece 16,18 to the next distal flat piece 18 or proximal flat piece 16, respectively. In this embodiment, the resulting "ridge" 13, when viewed in cross-section, resembles an isosceles triangle, flat pieces 16,18 being the isosceles legs of the triangle.

Figure 5:
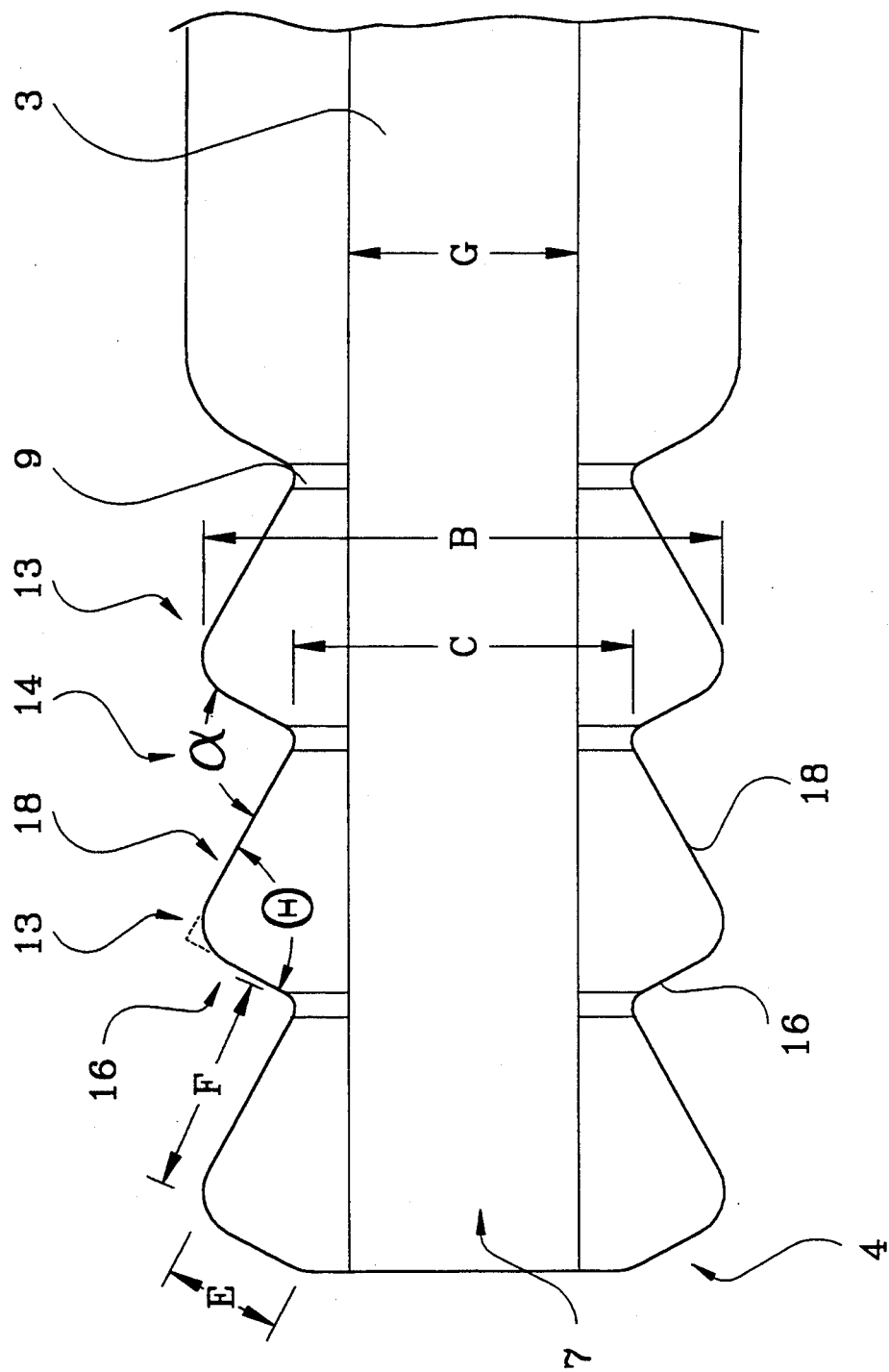
FIG. 5 is a cross-sectional view of the proximal end of the catheter according to another embodiment of the present device.
Figure 6:
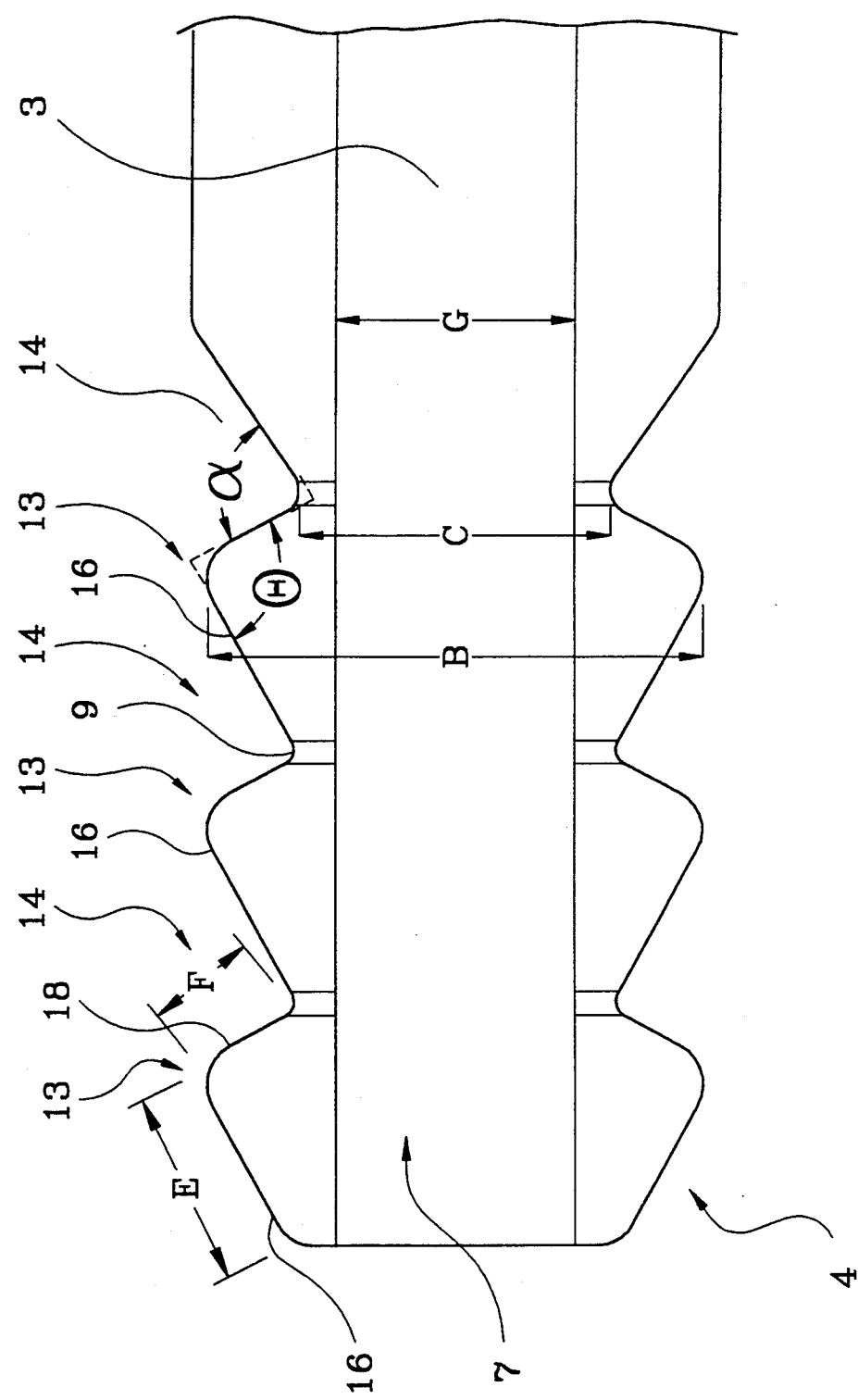
FIG. 6 is a cross-sectional view of an alternate embodiment of the catheter of the present invention.

However, in alternate embodiments shown in FIGS. 5 and 6, the width E of proximal flat pieces 16 is more or less, respectively, than the width F of distal flat pieces 18. In these embodiments, instead of "ridges" 13 resembling isosceles triangles in cross-section, scalene triangles are formed.

In the preferred embodiment, the main lumen 3 of the catheter 1 extends through the bellowed tubular part 11 to the proximal end 4 at the same diameter G as the lumen 3 has in the straight tubular part 12. In this embodiment, the area between flat pieces 16,18 in "ridges" 13 is filled with the material of the catheter so that the "ridges" 13 are solid pieces. In this embodiment, the "major" and "minor" diameters B,C of the bellowed tubular part 11 have constant values for the entire length of the bellowed tubular part 11.

Figure 7:
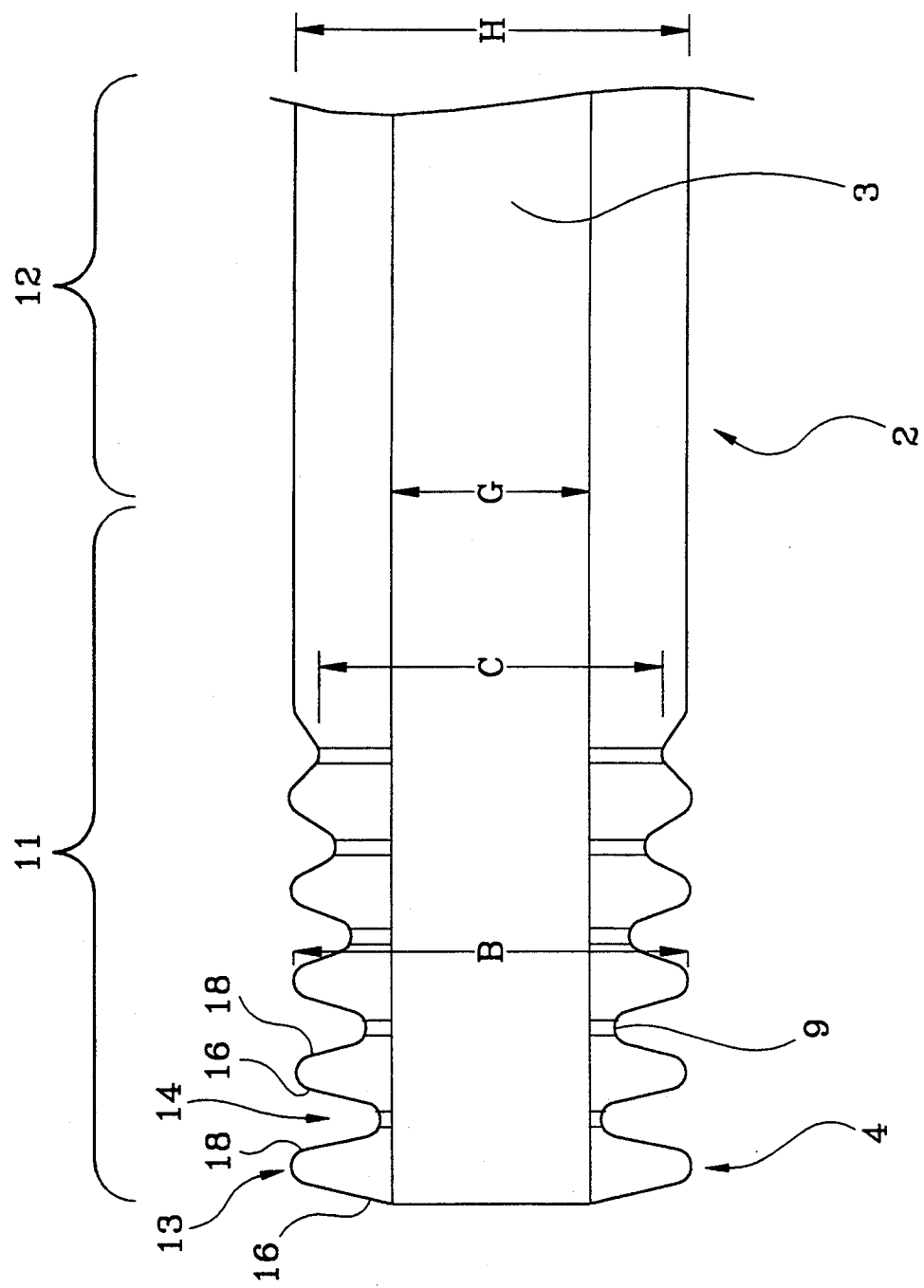
FIG. 7 is a cross-sectional view of another alternate embodiment of the catheter of the present invention.

In an alternate embodiment shown in FIG. 7, the "major" diameter B of the bellowed tubular part 11 remains constant at approximately the outer diameter of the straight tubular part 12 but the "minor" diameter C of the tubular bellowed part 11 gradually increases moving from the proximal end 4 toward the straight tubular part 12. In both embodiments shown in FIGS. 3 and 7, the diameter G of the lumen 3 extending through the tubular bellowed part 11 is approximately equal to the diameter G of the lumen 3 in the straight tubular part 12.

In this embodiment, because the "minor" diameter C of the bellowed tubular part 11 becomes larger as it nears the straight tubular portion 12 of the catheter 1, the proximal end 4 is made flexible while the rigidity of the catheter 1 gradually increases moving toward the straight tubular portion 12. Consequently, it is possible to provide a suction catheter 1 which doesn't bend and twist during insertion of the catheter 1 into the body lumen A.

This embodiment allows the portion of the catheter 1 near the opening 7 of the proximal end 4 to have a large flexibility while the stiffness of the bellowed tubular part 11 increases approaching straight tubular part 12 from the opening 7. The result of such construction is to improve the catheter's ability to prevent mucous membranes from injury because of the flexibility of proximal end 4 while still allowing the catheter 1 to be moved and rotated due to the stiffness of the bellowed tubular part 11 near the straight tubular part 12 in order to position the catheter 1.

In the preferred embodiments shown in FIGS. 3 through 7 both the diameter G of lumen 3 and "major" diameter B of the bellowed tubular portion 11 are substantially identical with the diameter G and outer diameter H f the lumen 3 and the straight tubular part 12, respectively. By maintaining a virtually constant diameter G along lumen 3 from the straight tubular part 12 through the bellowed tubular part 11 to the distal end 5, the vacuum pressure present in lumen 3 is unaffected by the presence of the bellowed tubular part 11.

In addition, because the major diameter B of the bellowed tubular part 11 is made almost identical with the outer diameter H of the straight tubular part 12, no restriction is given along the whole outer diameter of the catheter 1 because of the bellowed tubular part 11. As a result of the identical diameters G,H of both the lumen 3 and the outer surface of catheter 1 through both the straight part 12 and bellowed tubular part 11, the air flow pattern through and around the suction catheter 1 is substantially the same as that of the conventional catheters such as those shown FIG. 1, despite the presence of the bellowed tubular part 11. This allows the suction catheter to attain a good suction efficiency.

Figure 3A:
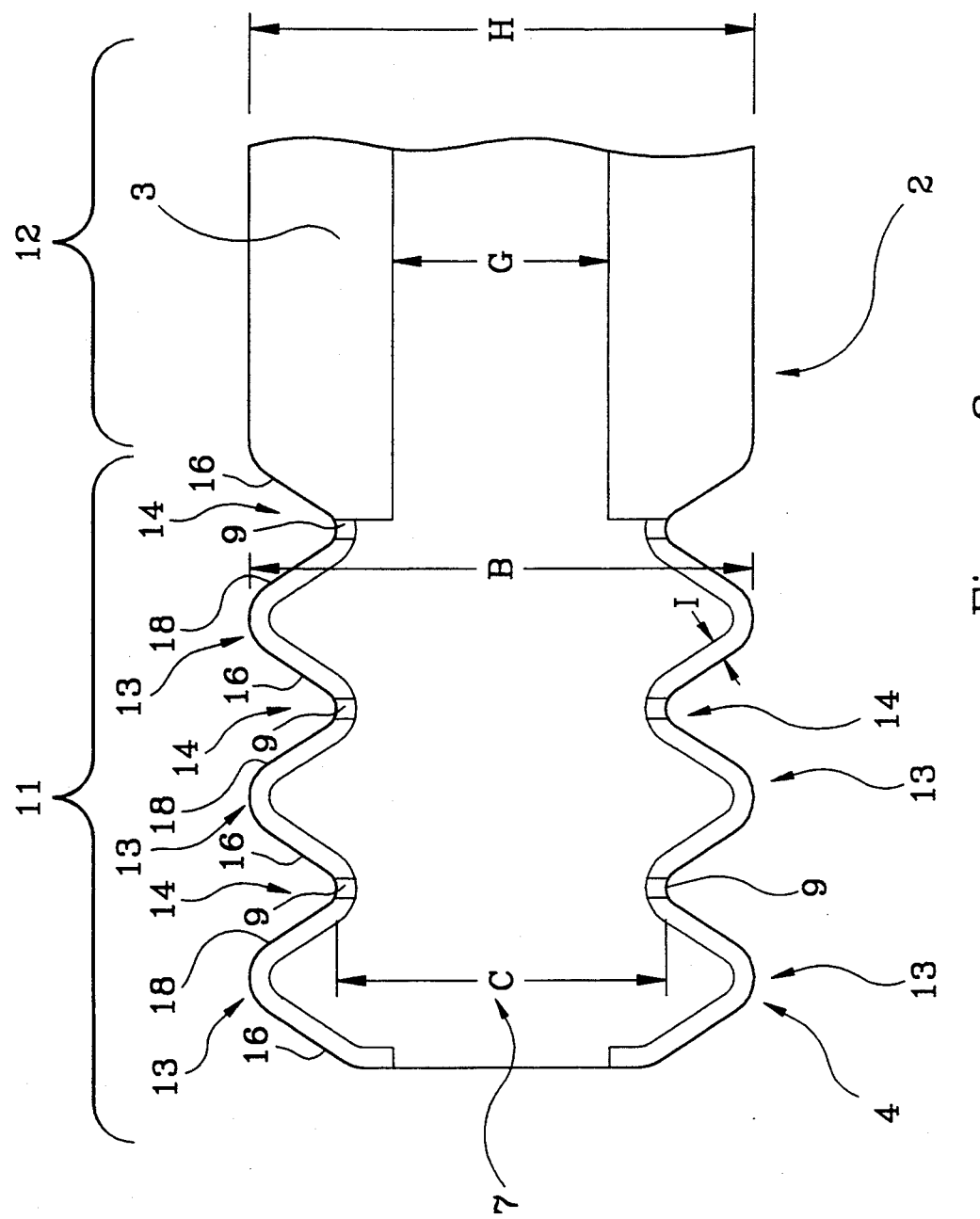
FIG. 3a is a cross-sectional view of an alternate embodiment of the catheter of FIG. 3.
Figure 5A:
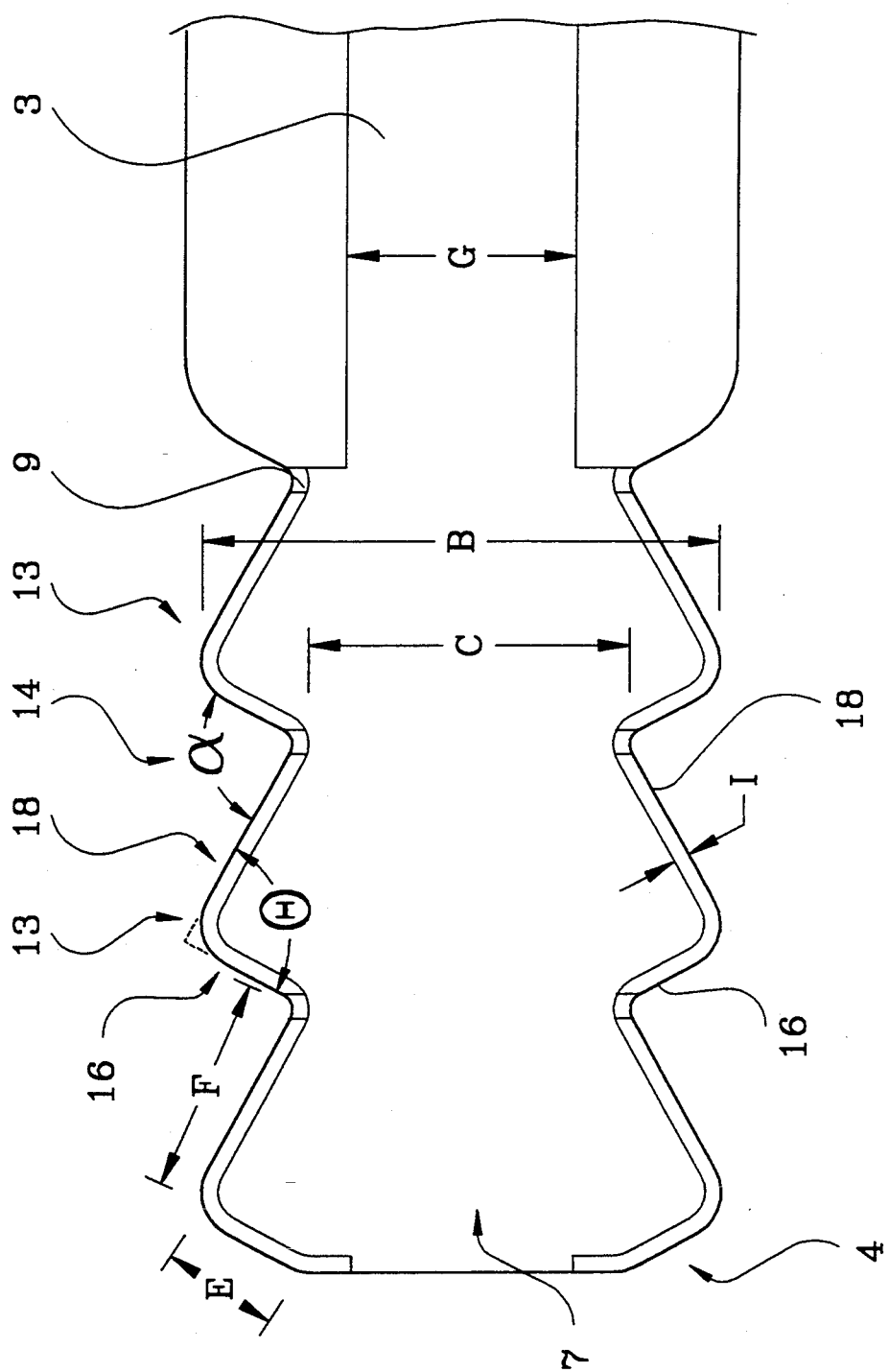
FIG. 5a is a cross-sectional view of an alternate embodiment of the catheter of FIG. 5.
Figure 6A:
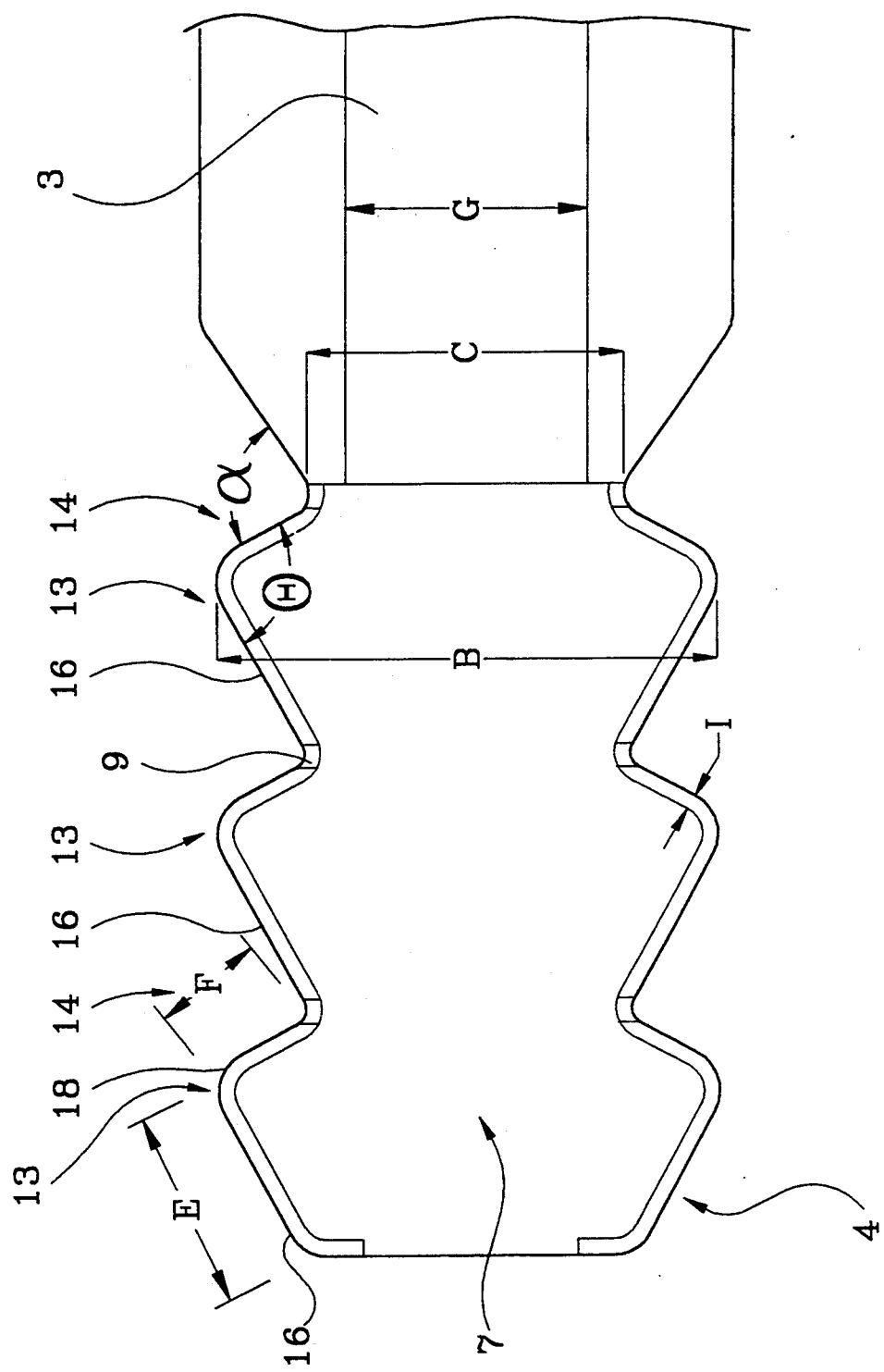
FIG. 6a is a cross-sectional view of an alternate embodiment of the catheter of FIG. 6.

In alternate embodiments shown in FIGS. 3a, 5a and 6a, the flat side pieces 16,18 of the "ridges" 13 each have a fixed thickness I along substantially their entire width. Thickness I (shown in FIGS. 3a, 5a and 6a, as greatly exaggerated) is preferably thin to allow flat pieces 16,18 to flex at their connecting edges. In these embodiments, the diameter G of the lumen 3 in the bellowed tubular part 11 will be the "minor" diameter C of the bellowed tubular part 11. In these embodiments, flat pieces 16,18 will flex around their connecting points to each other so that angles $\theta$ and $\alpha$ will change. As the bellowed tubular part 11 is compressed or stretched from its relaxed configuration, the changing angles $\theta$ and $\alpha$ will cause the "minor" diameter C, and consequently the diameter G of the lumen 3 through the bellowed tubular part 11, to decrease or increase.

The increased or decreased "minor" diameter C will affect the vacuum pressure present in the bellowed tubular part 11 as vacuum pressure is applied to the main lumen 3 at the distal end 5 of the catheter 1. In this way, the vacuum pressure presented at the proximal end 4 of the catheter 1 may be varied by compressing or relaxing the bellowed tubular part 11 by moving the distal end 5 of the catheter 1 toward and away, respectively, from the proximal end 4 of the catheter 1 while the catheter 1 is in the body lumen A. This variable pressure, in combination with the variable pressure caused by covering and uncovering suction control hole 10, may assist in moving debris or other material into lumen 3 through end hole 7 and side holes 9.

Figure 9:
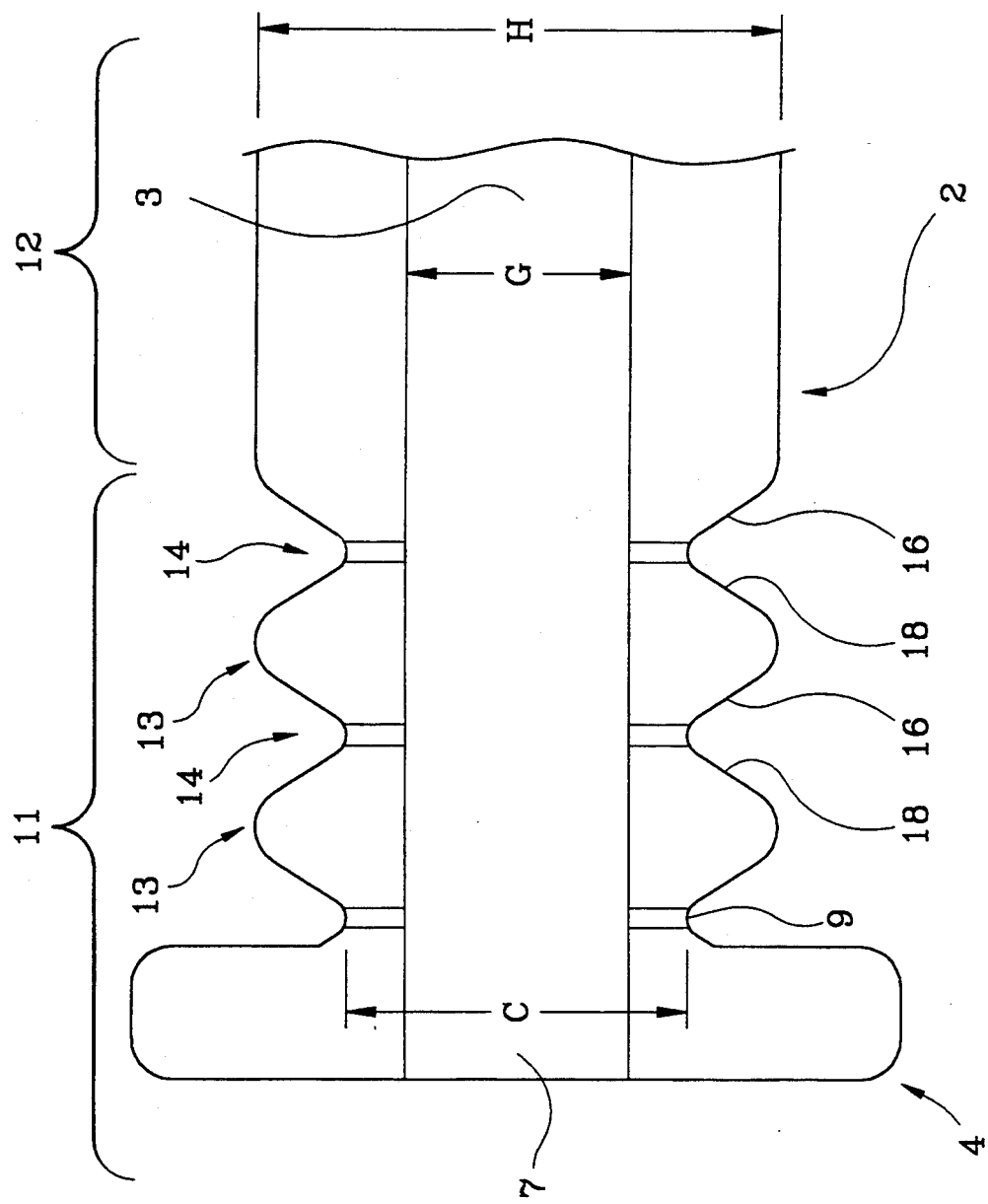
FIG. 9 is a cross-sectional view and another alternate embodiment of the catheter of the present invention.

In a variation of the embodiments described above as shown in FIG. 9, an annular flange 8 is located on the end of the proximal end 4 of the catheter 1. This flange 8 has a diameter larger than the outer diameter of the straight tubular part 12 or the major diameter B of the bellowed tubular part 11 and extends away from the proximal end 4 at a right angle to the axis of the catheter 1 at the proximal end 4.

In all the embodiments described above, an end hole 7 fluidly connects the most proximal end of lumen 3 with the exterior of the catheter 1 at proximal end 4. End hole 7 is aligned with the axis of lumen 3. End hole 7 preferably has a diameter approximately equal to the diameter of lumen 3 at proximal end 4 but may also have a larger or smaller diameter as desired.

In all the embodiments described above, several side holes 9 are preferably placed through the "valleys" 14 thereby fluidly connecting lumen 3 with the exterior of catheter 1. Although at least one side hole 9 is preferably placed on every "valley" 14, it is not necessary to place a side hole 9 on every "valley" 14. In addition, several side holes 9 may be placed on a single "valley" 14. Further, the number of the side holes 9 formed in each "valley" 14 may increase, decrease or remain constant moving away from the proximal end 4 toward the straight tubular part 12.

Figure 8:
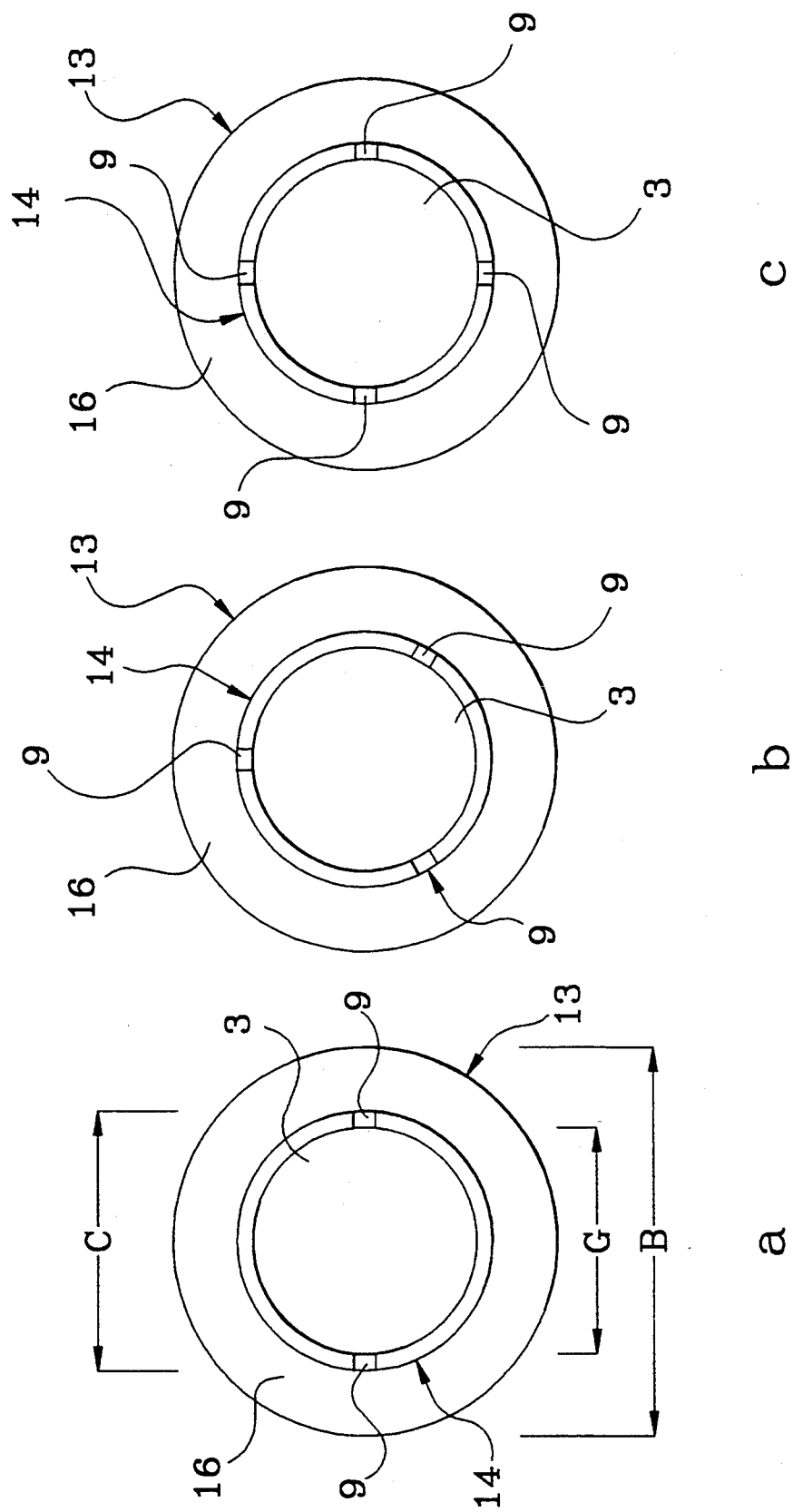
FIGS. 8a-c are cross-sectional views perpendicular to the elongated axis of the devices of FIGS. 3 and 4 showing the placement of the side holes.

FIGS. 8 a–c show cross-sectional views perpendicular to the central axis of suction catheter 1. As can be seen, the location of side holes 9 in the "valleys" 14 are preferably spaced around the central axis of suction catheter 1. FIGS. 8 a, b and c show the location of two, three and four side holes 9 respectively equally spaced around the central axis of suction catheter 1. Of course, only one side hole per "valley" 14 or more than four side holes per "valley" 14 may be positioned as desired. Further, although the preferred embodiment has side holes 9 equally spaced around the periphery of suction catheter 1, side holes 9 may be bunched in groups or not equally spaced as desired.

In addition, side holes 9 may be staggered from one "valley" 14 to an adjacent "valley" 14. Staggering means that side holes on adjacent "valleys" are not aligned along an axis parallel to the main axis of lumen 3, but are offset from each other. This staggered arrangement of side holes 9 may produce a wider dispersion of vacuum pressure along the outer surface of catheter 1 than would occur if the side holes 9 were not staggered.

As described above, according to the instant invention, the proximal end 4 of the suction catheter 1 is made of a bellowed tubular part 11 so that the proximal end 4 has an increased and desirable flexibility compared to prior catheters. Consequently, the proximal end 4 of the catheter 1 doesn't strike and hurt the trachea and bronchial tube when the catheter 1 is placed into or retained in position in the trachea or bronchial tube. In addition, the bellowed tubular part 11 does not decrease suction efficiency of the catheter.

In some cases, it is desirable to make a catheter 1 having the bellowed tubular part 11 according to the teachings of this disclosure, having a side hole or holes 9 but not having an end hole 7 or having an end hole 7 but not having any side holes 9.

In the embodiments described herein, the "major" diameter B of the bellowed tubular part 11 is made identical with that of the straight tubular part 12, so it is possible to freely select the suitable diameter of the catheter 1 according to the desired suction efficiency without compromising the suction efficiency of the catheter.

Although specific embodiments have been described herein, the number and angles $\theta$, $\alpha$ between the "ridges" 13 and "valleys" 14 of the bellowed tubular part 11 are not restricted to the specific embodiments described. In addition, the material of the catheter is not limited to PVC material but may encompass any suitable material for making such catheters as will be well understood by those in the art.

In operation, catheter 1 is inserted into a body lumen A of a patient. Vacuum pressure is provided to catheter 1 through lumen 3 at the distal end 5. When suction control hole 10 is closed, vacuum pressure is provided through lumen 3 to end hole 7 and side hole or holes 9. The pressure differential between body lumen A and lumen 3 causes air to move in body lumen A toward catheter 1. One part of the air will move toward and enter end hole 7. Another part of the air will move toward and enter side hole or holes 9.

The moving air will move debris or other articles from within body lumen A into lumen 3 through end hole 7 and side hole or holes 9. After the debris or other article is within lumen 3, vacuum pressure continues to move the debris or other article out of the catheter at the distal end 5.

The instant invention has been described in connection with specific embodiments. However, it is to be understood that the descriptions given herein have been given by means of example and not for the purpose of limiting the invention. Changes and modifications may be made to the description contained herein and still be within the scope of the invention. Further, obvious changes and modifications will occur to those skilled in the art.

We claim:

1. A suction catheter having a distal end and a proximal end to be inserted into a body, the catheter comprising:
   a) a tubular body having a main tubular body lumen extending from the proximal to the distal end of the tubular body;
   b) a bellowed tubular part attached to the proximal end of said tubular body, said bellowed tubular part comprising an alternating series of annular ridges and valleys surrounding a bellowed tubular part lumen extending from the proximal to the distal end of the bellowed tubular part, the bellowed tubular part lumen attached to and in fluid communication with said main tubular body lumen, each of said ridges formed by connecting an annular proximal flat piece to a distal flat pieces at an acute angle, said valleys formed by connecting, at an acute angle, a distal flat piece to an adjoining proximal flat piece where the central axes of adjoining ridges are aligned, whereby an alternating series of ridges and valleys is formed along the length of said bellowed tubular part, the width of said proximal flat pieces being different than the width of said distal flat pieces, whereby, each of said ridges has a cross-section resembling a scalene triangle" have been deleted and replaced by a triangular cross-section having sides of different lengths.

2. The catheter of claim 1 wherein said bellowed tubular part includes at least one side hole extending from said main lumen to one of said valleys thereby providing fluid communication from the exterior of the catheter to said main lumen through said side hole.

3. The catheter of claim 1 wherein said main lumen has an opening at the proximal end of the catheter substantially aligned with the axis of said main lumen and fluidly connecting the exterior of the catheter with said main lumen.

4. The catheter of claim 1 further comprising at least one opening extending through said bellowed tubular part from said main lumen to fluidly connect said main lumen to the exterior of said catheter.

5. The catheter of claim 4 wherein said opening or openings are formed through said valleys.

6. The catheter of claim 1 further comprising:
   a) said main lumen having an opening at the proximal end of the catheter substantially aligned with the axis of said main lumen and fluidly connecting the exterior of the catheter with said main lumen; and,
   b) at least one opening extending through said bellowed tubular part from said main lumen to fluidly connect said main lumen to the exterior of said catheter.

7. The catheter of claim 1 further comprising means for regulating the vacuum pressure within said tubular body lumen and said bellowed tubular part lumen.

8. The catheter of claim 1 further comprising hand manipulating means connected to the catheter at the distal end of the catheter.

9. The suction catheter of claim 1 wherein each of said flat pieces has a substantially constant thickness.

10. The suction catheter of claim 1 further comprising an annular flange attached to the proximal end of said bellowed tubular body.

11. A suction catheter having a distal end and a proximal end to be inserted into a body, the catheter comprising:
   a) a tubular body having a main lumen extending from the proximal to the distal end of the catheter;
   b) a bellowed tubular part located at the proximal end of the catheter, said bellowed tubular part comprising an alternating series of annular ridges and valleys located at the proximal end of the catheter, each of said annular peaks having a major diameter, each of said valleys having a minor diameter, the major diameter remaining constant along at least a portion of said bellowed tubular part while the minor diameter gradually increases in a proximal direction over the part of said bellowed tubular part where the major diameter is constant.

12. The suction catheter of claim 11 wherein the diameter of said main lumen of said tubular body has substantially the same diameter as the diameter of the diameter of said main lumen in said bellowed tubular body.

13. The suction catheter of claim 11 wherein the outer diameter of said tubular body is approximately equal to the major diameter of said tubular body.

14. The suction catheter of claim 11 wherein each of said flat pieces has a substantially constant thickness.

15. The suction catheter of claim 11 wherein the cross-sectional area of each of said ridges is comprised of a solid material.

16. The suction catheter of claim 11 further comprising an annular flange attached to the proximal end of said bellowed tubular body.

* * * * *

UNITED STATES PATENT AND TRADEMARK OFFICE
CERTIFICATE OF CORRECTION

PATENT NO. : 5,431,637
DATED : July 11, 1995
INVENTOR(S) : Okada, et al.

It is certified that error appears in the above-indentified patent and that said Letters Patent is hereby corrected as shown below:

Column 8, line 10, delete -- a cross-section resembling a scalene triangle --.

Column 8, line 11, delete -- have been deleted and replaced by --.

Signed and Sealed this

Seventeenth Day of October, 1995

BRUCE LEHMAN

*Attest:*

*Attesting Officer*        *Commissioner of Patents and Trademarks*